(12) United States Patent
Schneider et al.

(10) Patent No.: US 6,808,514 B2
(45) Date of Patent: Oct. 26, 2004

(54) EMERGENCY MEDICAL DISPENSING CARD

(76) Inventors: Patricia G. Schneider, 33 Aspen Cir., Albany, NY (US) 12208; Robert M. Schneider, P.O. Box 60, Tannersville, NY (US) 12485

( * ) Notice: Subject to any disclaimer, the term of this patent is extended or adjusted under 35 U.S.C. 154(b) by 402 days.

(21) Appl. No.: 09/981,372

(22) Filed: Oct. 17, 2001

(65) Prior Publication Data

US 2002/0074345 A1 Jun. 20, 2002

Related U.S. Application Data

(60) Provisional application No. 60/241,090, filed on Oct. 17, 2000, provisional application No. 60/264,939, filed on Jan. 29, 2001, and provisional application No. 60/262,596, filed on Jan. 17, 2001.

(51) Int. Cl.[7] .............................................. A61M 5/00
(52) U.S. Cl. ........................................................ 604/232
(58) Field of Search ................................ 604/191, 192, 604/208, 218, 232, 234, 240, 131, 187, 189, 198, 227, 228, 197

(56) References Cited

U.S. PATENT DOCUMENTS

| | | | | |
|---|---|---|---|---|
| 3,702,608 A | * | 11/1972 | Tibbs | 604/136 |
| 4,690,676 A | | 9/1987 | Moulding, Jr. et al. | 604/189 |
| 4,781,696 A | * | 11/1988 | Moulding, Jr. et al. | 604/189 |
| 4,923,447 A | * | 5/1990 | Morgan | 604/198 |
| 5,186,712 A | * | 2/1993 | Kelso et al. | 604/165.03 |
| 5,397,017 A | | 3/1995 | Muza et al. | 221/91 |
| 5,443,178 A | | 8/1995 | Holmes | 221/64 |
| 5,556,599 A | | 9/1996 | Ahmed | 422/102 |
| RE35,986 E | | 12/1998 | Ritson et al. | 604/88 |
| 5,954,643 A | * | 9/1999 | VanAntwerp et al. | 600/316 |
| 5,980,506 A | * | 11/1999 | Mathiasen | 604/535 |
| 6,024,221 A | | 2/2000 | Yuyama et al. | 206/528 |
| 6,032,411 A | * | 3/2000 | Foust | 47/57.5 |
| 6,102,896 A | * | 8/2000 | Roser | 604/218 |
| 6,123,690 A | * | 9/2000 | Mejslov | 604/533 |
| 6,210,369 B1 | | 4/2001 | Wilmot et al. | 604/157 |
| 6,224,567 B1 | * | 5/2001 | Roser | 604/68 |
| 6,302,866 B1 | * | 10/2001 | Marggi | 604/174 |
| 6,447,485 B2 | * | 9/2002 | Bierman | 604/174 |
| 6,488,663 B1 | * | 12/2002 | Steg | 604/164.08 |
| 6,520,938 B1 | * | 2/2003 | Funderburk et al. | 604/164.08 |
| 6,572,586 B1 | * | 6/2003 | Wojcik | 604/165.01 |
| 6,602,222 B1 | * | 8/2003 | Roser | 604/68 |
| 2002/0013522 A1 | * | 1/2002 | Lav et al. | 600/365 |
| 2003/0212362 A1 | * | 11/2003 | Rosar | 604/110 |

* cited by examiner

*Primary Examiner*—Anhtuan T. Nguyen
(74) *Attorney, Agent, or Firm*—Mark S. Leonardo; Peter B. Sorell; Brown Rudnick Berlack Israele LLP

(57) ABSTRACT

A therapeutic dispenser is provided that includes a housing and a carriage movably supported by the housing and including an engagement surface at a distal end thereof. A plunger is supported by the carriage and engageable with the housing to dispense a first therapeutic through the engagement surface. A second therapeutic is supported with the housing. The first therapeutic and the second therapeutic are individually dispensable from the housing. The housing may include a channel that guides movement of the carriage. The housing can include a handle and a cap. The cap is releasably engageable with the handle.

8 Claims, 16 Drawing Sheets

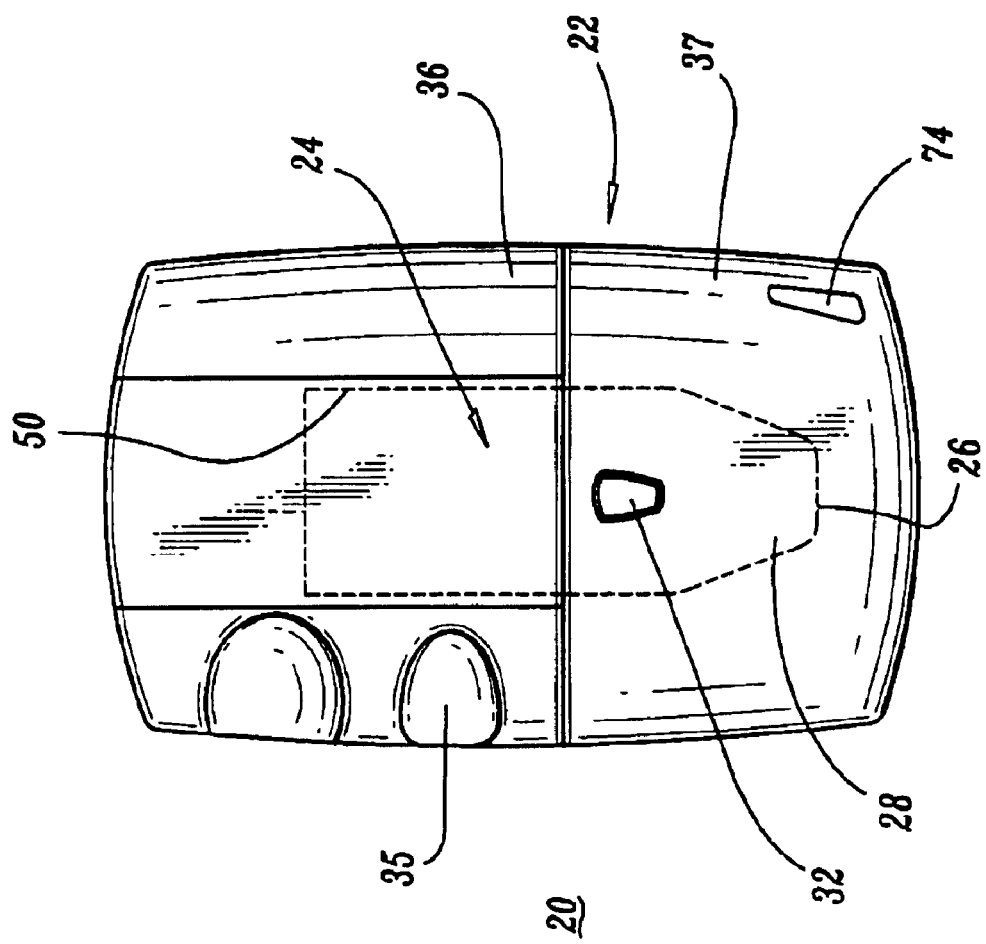

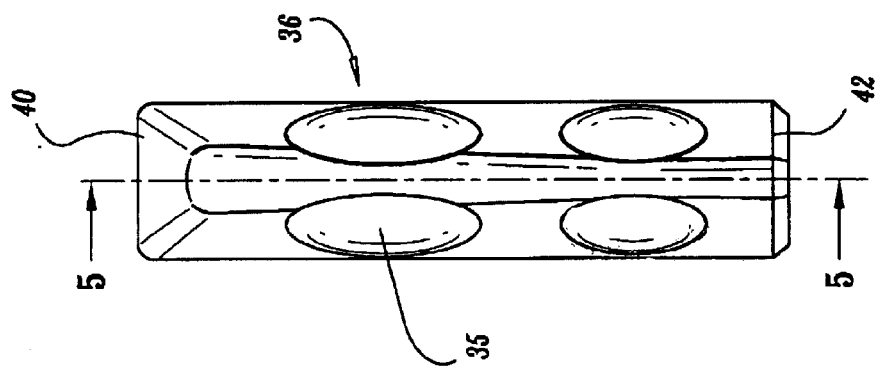
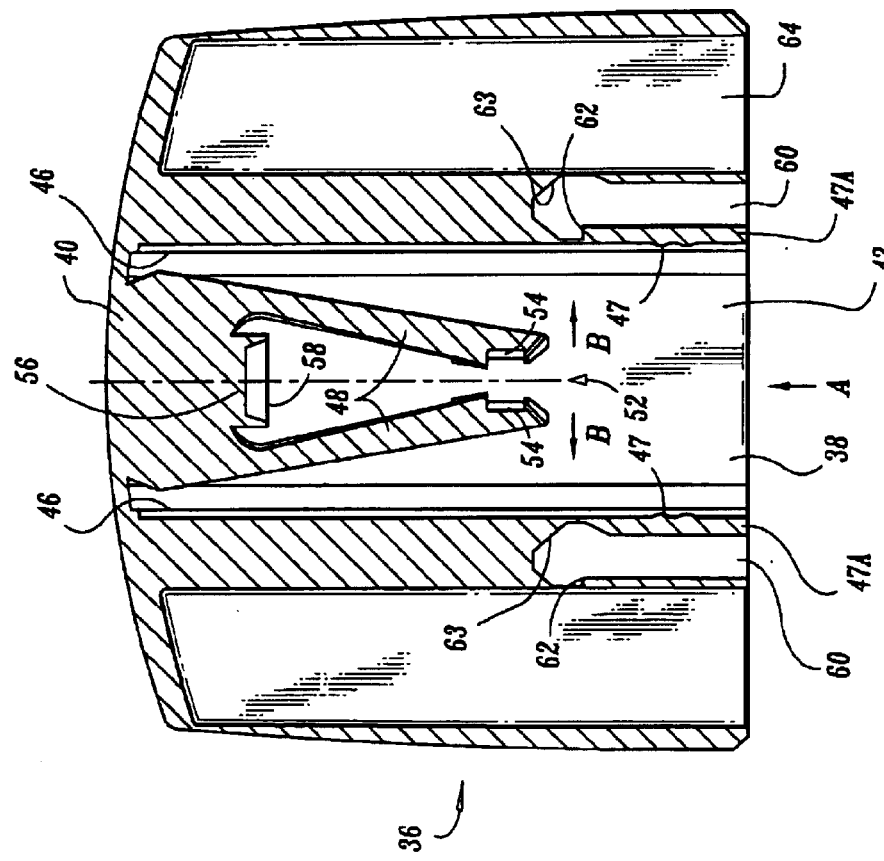

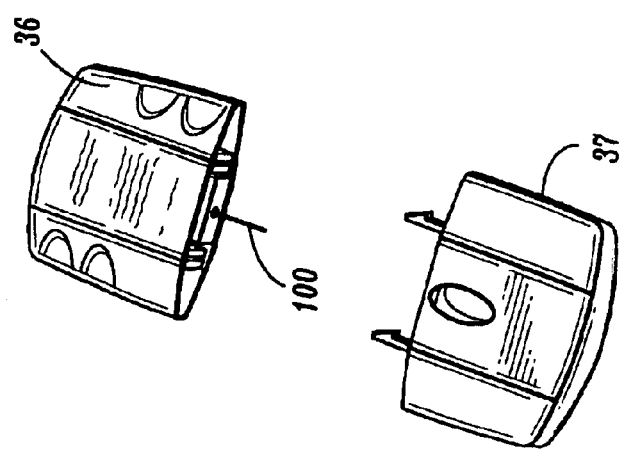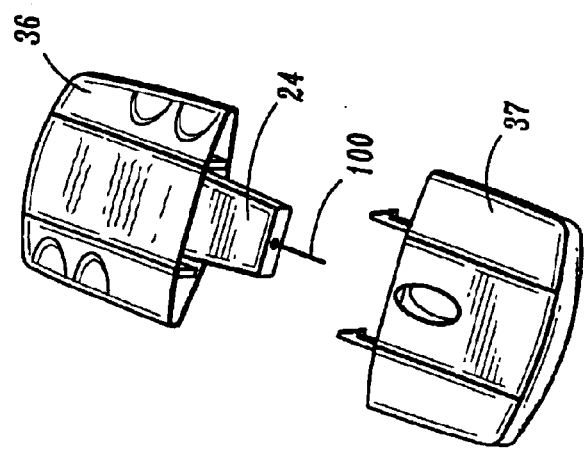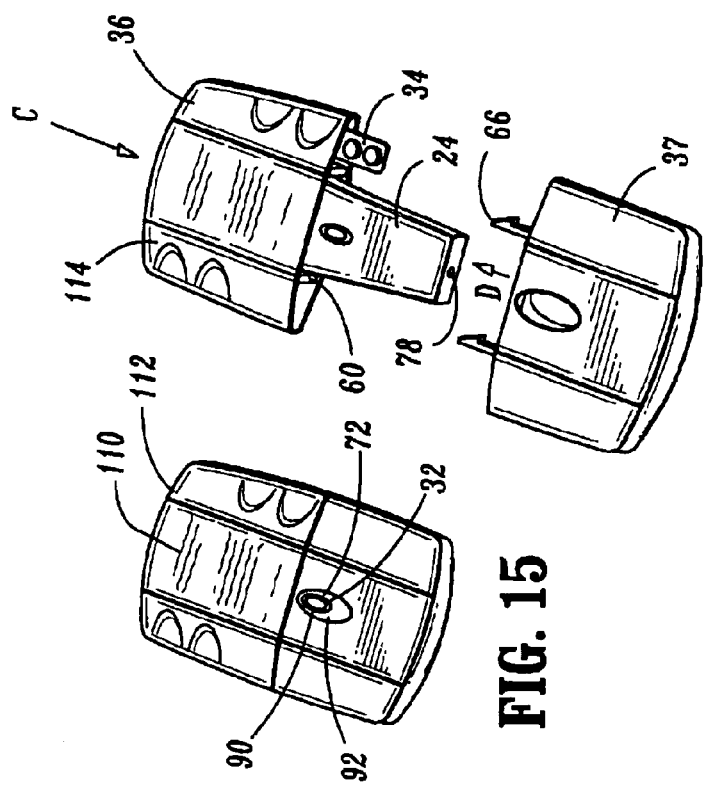

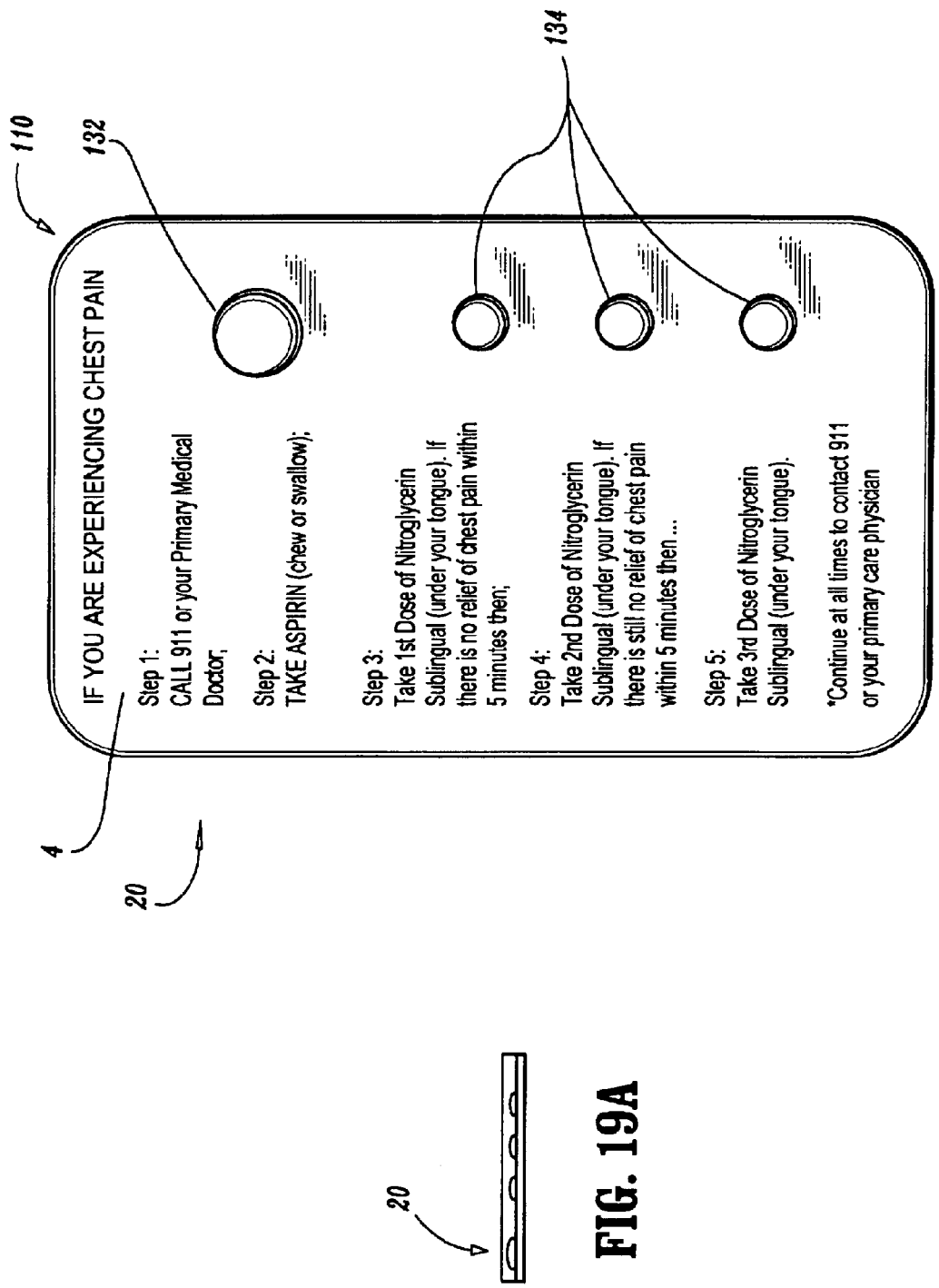

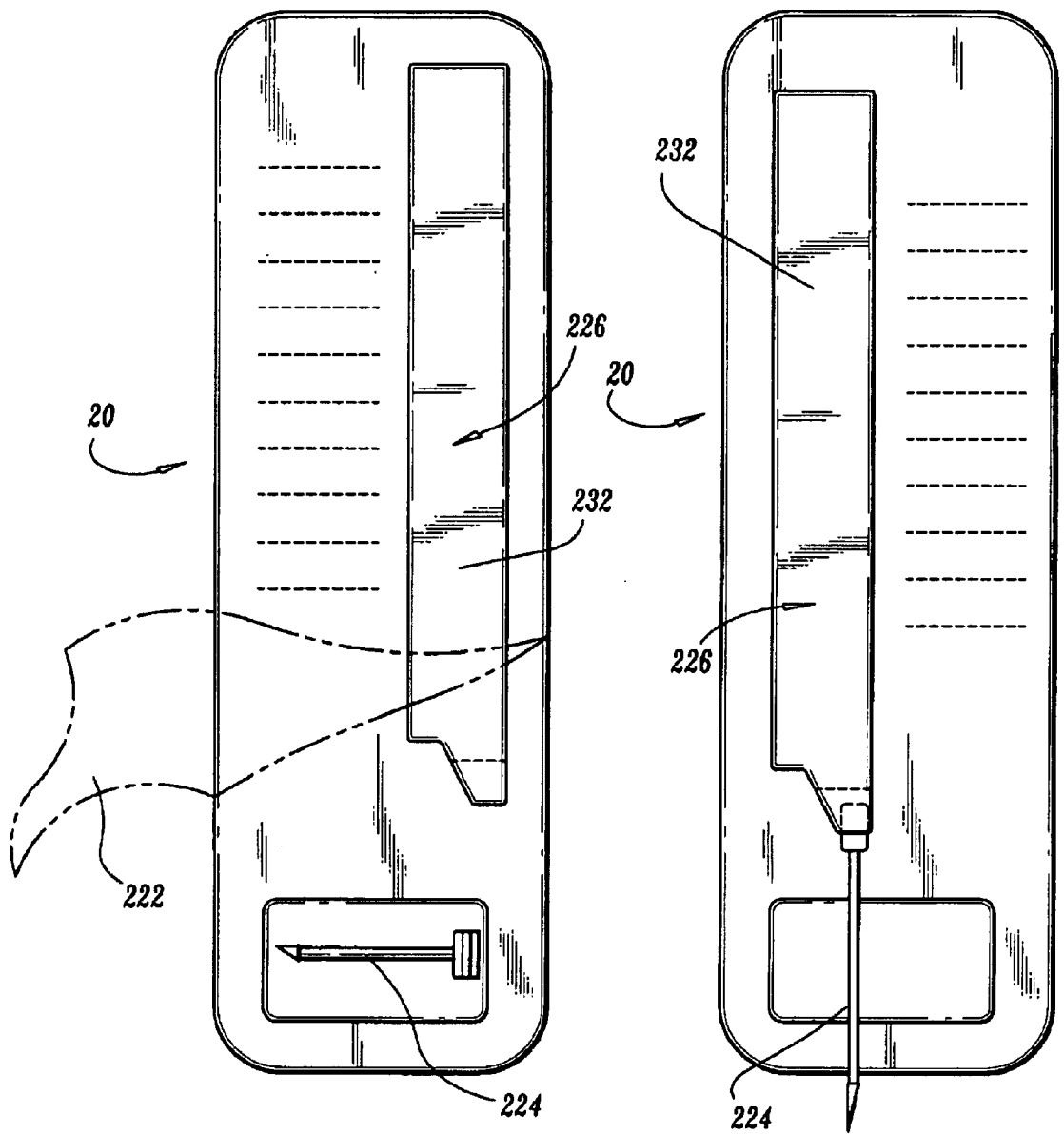

EMERGENCY MEDICAL DISPENSING CARD

CROSS-REFERENCE TO RELATED APPLICATIONS

This patent application claims priority to U.S. Provisional Application Ser. No. 60/241,090, filed in the U.S. Patent and Trademark Office (USPTO) on Oct. 17, 2000 by Schneider et al., U.S. Provisional Application Ser. No. 60/264,939 filed in the USPTO on Jan. 29, 2001 by Schneider et al., and U.S. Provisional Application Ser. No. 60/262,596 filed in the USPTO on Jan. 17, 2001 by Schneider et al., the entire contents of each of these applications being hereby incorporated by reference herein.

BACKGROUND

1. Technical Field

The present disclosure relates to therapeutic dispensing devices, and more particularly to a therapeutic dispenser that supports a first or plurality of therapeutics to be dispensed individually.

2. Description of the Related Art

Frequently, when an individual suffers from a medical episode, such as severe allergic reaction of a bee sting, food ingestion, early signs of angina, etc., the medication, such as, for example, chemicals, therapeutics, preventive medicines, etc., that may save their life are not readily available. Even in those cases when an individual may have their medication, instructions for their proper administration may not be readily available or may be contained on a document not with the medication, requiring a search. During such episodes, any time wasted searching for the medication or the instructions may be critical to the individual.

For example, individuals that are at a high risk of suffering from angina pectoris are prescribed and instructed to take an aspirin followed by three doses of nitroglycerin at a prescribed time frame. The patient is given a prescription for the nitroglycerin, which is then purchased from a pharmacist. The aspirin can be purchased over the counter in various forms. Typically both forms of medication are provided in tablet form and supplied from a container, typically in a bottle design. Disadvantageously, such bottles are not, even if small, conducive to carrying around on your person. Further, two separate bottles for the dispensing of the individual medications are even more cumbersome.

Another drawback of the current state of the art is that typical instructions for the administration of these medications during such an episode is contained on a separate document that is carried with the two drugs. Thus, the individual may be required to carry at least four items on their person.

Thus, in an emergency or if an individual believes they are suffering from the early signs of a heart attack, the individual is forced to manipulate and understand the several items carried while enduring some degree of panic and physical pain. The medication may not be readily available. Even if the medication is available, the instructions for their administration may not be available or would require a search to be found.

Therefore, it would be highly desirable to have a self-contained therapeutic dispenser that supports a first therapeutic and a second therapeutic that are dispensed individually from the therapeutic dispenser which is employed in a facile manner.

Accordingly, it is one object of the present disclosure to provide a self-contained therapeutic dispenser that supports at least a first therapeutic and a second therapeutic that are dispensed individually from the therapeutic dispenser which is employed in a facile manner.

It is a further object of the present disclosure to provide a therapeutic dispenser that is easily activated to dispense a therapeutic via engagement of the therapeutic dispenser with a body surface of an individual.

It is also an object of the present disclosure to provide a therapeutic dispenser that displays instructional indicia that can be easily viewed during operation.

It is yet another object of the present disclosure to provide a therapeutic dispenser which is efficiently and inexpensively manufactured and assembled.

Objects and advantages of the present disclosure are set forth in part herein and in part will be obvious therefrom, or may be learned by practice of the present disclosure, which is realized and attained by means of the instrumentalities and combinations pointed out in the appended claims. The apparatus and methods of the present disclosure consists of novel parts, constructions, arrangements, combinations, steps and improvements herein shown and described.

SUMMARY

In accordance with the principles of the present disclosure, there is provided a therapeutic dispenser. One of the objects of the present disclosure is to provide a therapeutic dispensing card comprising a single or a plurality of therapeutics and/or small medical devices and instructions for the administration of the therapeutics and/or small medical device contained on the face, back or within the card. The card has a dimension that is suitable for an individual to carry on their person. For example, the card could have the dimensions of a credit card and be carried in a shirt or pant pocket or be attached to a chain that is worn around the neck. The card is useful in emergency situations such as when an individual believes that they are suffering from the early stages of a heart attack, a serious allergic reaction, etc.

In one particular embodiment, in accordance with the present disclosure, a therapeutic dispenser is provided. The therapeutic dispenser includes a housing and a carriage movably supported by the housing and including an engagement surface at a distal end thereof. A plunger is supported by the carriage and engageable with the housing to dispense a first therapeutic through the engagement surface. A second therapeutic is supported with the housing. The first therapeutic and the second therapeutic are individually dispensable from the housing. This configuration advantageously provides a self-contained therapeutic dispenser that supports a plurality of therapeutics dispensed individually from a device which is employed in a facile manner. It is contemplated that the therapeutic dispenser may alternatively combine a plurality of therapeutics for dispensing in, for example, one injection.

The housing may include a channel that guides movement of the carriage. The housing may include a pusher. The housing can releasably retain the carriage in an extended position. Desirably, the housing is configured and dimensioned as a card. The housing may include instructional indicia. The housing and the carriage may provide visual indicia of the first therapeutic.

In an alternate embodiment, the housing includes a handle and a cap. The cap is releasably engageable with the handle. The handle may define at least one receiving cavity which is releasably engageable with at least one pin of the cap. The at least one pin can define an arrestor actuator that engages the handle to facilitate disengagement of the cap and the handle.

The housing may define a cavity for support of the second therapeutic. The carriage may support a needle that extends through an opening of the engagement surface. The needle can include a barrel that supports the plunger. The barrel includes a needle hub having a needle cannula extending through the opening. The first therapeutic may be disposed in the barrel.

In another alternate embodiment, the engagement surface is substantially non-flexible. The engagement surface may define an opening for dispensing the first therapeutic therethrough. The engagement surface may be configured to engage a body surface such that the plunger engages the housing to dispense the first therapeutic from the carriage and through the engagement surface.

BRIEF DESCRIPTION OF DRAWINGS

The objects and features of the present disclosure, which are believed to be novel, are set forth with particularity in the appended claims. The present disclosure, both as to its organization and manner of operation, together with further objectives and advantages, may be best understood by reference to the following description taken in connection with the accompanying drawings wherein:

FIG. 1 is a front view of one particular embodiment of a therapeutic dispenser, in accordance with the principles of the present disclosure, showing a carriage in phantom;

FIG. 2 is a side view of the therapeutic dispenser shown in FIG. 1;

FIG. 4 is a side view of the handle shown in FIG. 3;

FIG. 5 is a cross-sectional view of the handle taken along lines 5—5 of FIG. 4;

FIG. 15 is a front perspective view of another embodiment of the therapeutic dispenser;

FIG. 16 is a front perspective view of the therapeutic dispenser, showing the carriage in an extended position;

FIG. 17 is a front perspective view of the therapeutic dispenser, showing the carriage in a partially retracted position;

FIG. 18 is a front perspective view of the therapeutic dispenser, showing the carriage in a fully retracted position;

FIG. 19 is a front view of another embodiment of the therapeutic dispenser having instructional indicia;

FIG. 19A is a side view of the therapeutic dispenser shown in FIG. 19;

FIG. 20 is a front view of another embodiment of the therapeutic dispenser

FIG. 21 is a front view of the therapeutic dispenser shown in FIG. 20 in an assembled position;

DETAILED DESCRIPTION OF THE EXEMPLARY EMBODIMENTS

Figure 7:
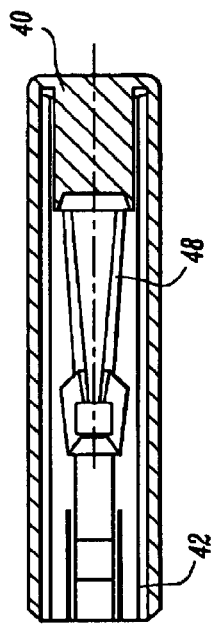
FIG. 7 is a cross-sectional view of the handle taken along lines 7—7 of FIG. 6.
Figure 6:
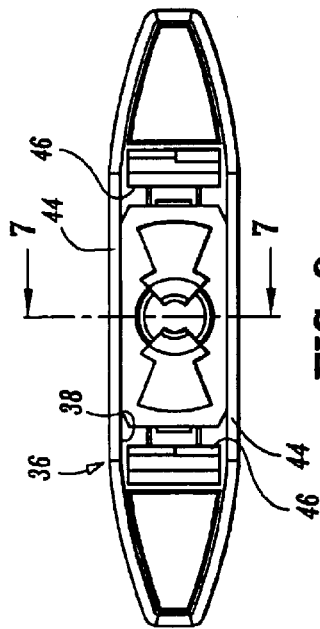
FIG. 6 is a bottom view of the handle shown in FIG. 3.
Figure 3:
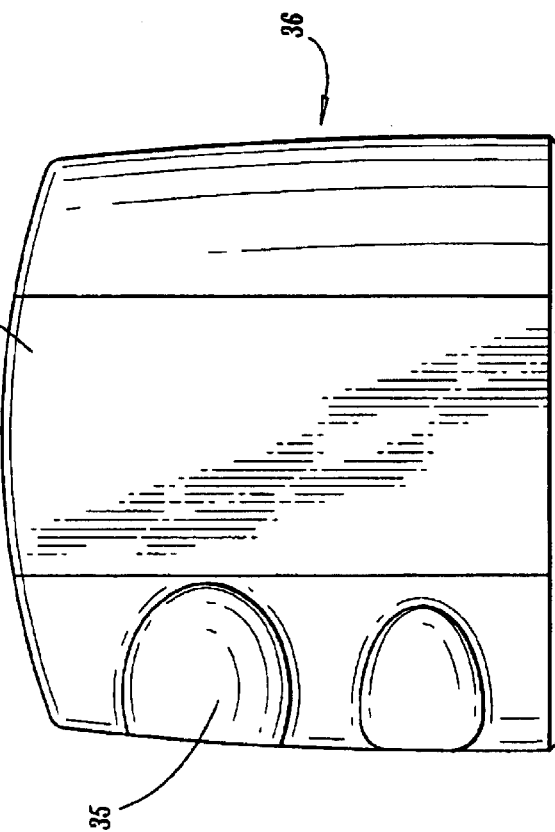
FIG. 3 is an enlarged front view of a handle of the therapeutic dispenser shown in FIG. 1.

The exemplary embodiments of the therapeutic dispenser and methods of operation disclosed are discussed in terms of therapeutic dispensing devices used to dispense medication including therapeutics, medications, etc., to a body of a subject for the treatment of disease or disorders, and more particularly, in terms of a portable dispenser which is low profile and suitable for the subject to carry. It is envisioned that the therapeutic dispenser may be carried in a shirt, pant pocket, wallet, purse, etc., of the subject or attached to a jewelry, chain, etc., worn by the subject. The therapeutic dispenser suitably finds application in emergency situations such as, for example, the early stages of a heart attack, serious allergic reactions, etc. It is contemplated that such a therapeutic dispenser may also be used for preventative medical applications whereby dispensing of medication serves a malady preventing function. It is further contemplated that the therapeutic dispenser may be employed for dispensing various forms of medication, such as, oral, topical, subcutaneous, intramuscular, etc. Such therapeutics, medications, etc., may include aspirin, nitroglycerin, antiacid, steroids, glucose, epinephrine, insulin, saline, (including bronchial), burn cream, antibiotics, (including oral, topical and subcutaneous forms), anti-venoms (including oral and subcutaneous forms), analgesics, anaphylaxis, etc. It is contemplated that the therapeutics, medications, etc., may include a plastic blister pack wherein the therapeutic is contained in a plastic or foil cavity. The therapeutic is obtained by pushing it through a foil or paper backing.

In the discussion which follows, the term "distal" will refer to the portion of the structure adjacent to injection site, while the term "proximal" will refer to an opposing portion of the structure. As used herein, the term "subject" refers to an individual including human, animal, etc., which receives medication via the therapeutic dispenser. "Injectable therapeutic" refers to any drug in any form that can be injected through a hypodermic needle. For example, insulin in the form of a liquid or gel with low viscosity.

The component parts of the therapeutic dispenser may be fabricated from materials suitable for dispensing therapeutics, medications, etc., or related medical procedures, such as, for example, polymerics or metals, such as stainless steel, depending on the particular medical application. Semi-rigid and rigid polymerics are contemplated for fabrication of particular components, as well as resilient materials, such as molded medical grade polypropylene, etc. One skilled in the art, however, will realize that other materials and fabrication methods suitable for assembly and manufacture, in accordance with the present disclosure, also will be appropriate.

Reference will now be made in detail to the exemplary embodiments of the present disclosure which are illustrated in the accompanying figures. Turning now to the figures, wherein like components are designated by like reference numerals throughout the several views and initially to FIGS. 1 and 2, there is illustrated a therapeutic dispenser 20, in accordance with the principals of the present disclosure.

Therapeutic dispenser 20 includes a housing 22 and a carriage 24 supported thereby. Carriage 24 includes an engagement surface 26 at a distal end 28. A plunger 30 (FIG. 13) is supported by carriage 24 and engageable with housing 22 to dispense a first therapeutic 32 through engagement surface 26, as will be discussed below in more detail. A second therapeutic 34 is supported with housing 22 such that first therapeutic 32 and second therapeutic 34 are individually dispensed from housing 22. This configuration advantageously provides a subject (not shown) with a portable, low profile therapeutic dispenser for administration of therapeutics in, for example, emergency situations which is employed in a facile manner. It is contemplated that therapeutic dispenser 20 may have monolithically formed component parts or that such component parts may be integrally assembled therewith, in accordance with the principles of the present disclosure and depending on the requirements of a particular therapeutic dispensing application. It is further contemplated that one or a plurality of therapeutics may be dispensed from therapeutic dispenser 20. It is envisioned that therapeutic dispenser 20 may alternatively combine a plurality of therapeutics for dispensing in, for example, one injection.

Referring to FIGS. 3–7, housing 22 includes a handle 36 and a cap 37. Handle 36 and cap 37 each have a substantially low-profile design whereby their respective widths are substantially greater than their thickness. Handle 36 releasably lockingly engages cap 37 to enclose carriage 24. Thus, housing 22 and therapeutic dispenser 20 have a card configuration whereby the card could have the dimensions of a conventional credit card or the like. For example, the dimensions would be suitable for carrying therapeutic dispenser 20 in the subject's shirt pocket, wallet, pant pocket, purse, briefcase, etc. Suitable dimensions include those of a conventional credit card, typically about 3¼ inches (8½ centimeters) by 2¼ inches (5½ centimeters). Other dimensions are also envisioned. It is contemplated that therapeutic dispenser 20 could be attached to a chain and worn around the neck or contained within a pouch to be attached to the subject via a lanyard 74. This advantageously facilitates employment of therapeutic dispenser 20 for dispensing a therapeutic in an emergency situation. Therapeutic dispenser 20 includes finger grips 35 for manipulation thereof.

Handle 36 defines a channel 38 centrally disposed along the width of handle 36. Channel 38 extends along the longitudinal length of handle 36 from a proximal end 40 to a distal end 42. Channel 38 is positioned to provide stability and ease of manipulation by the subject (not shown) during administration of a therapeutic from therapeutic dispenser 20. Channel 38 is configured for slidable movement of carriage 24 (FIG. 10) therein. It is contemplated that channel 38 may be alternatively disposed adjacent the sides of handle 36, off center, etc.

Channel 38 is defined by side walls 44 and inner walls 46 of handle 36. Walls 44 and 46 are configured to enclose carriage 24 for slidable movement therein. Carriage 24 engages walls 44 and 46 with a minimal amount of friction to facilitate slidable movement. It is contemplated that portions of walls 44 and 46 may not contact carriage 24 during slidable movement. It is also contemplated that carriage 24 may include a tooth and gear arrangement, ridges, etc., to facilitate movement of carriage 24 according to the requirements of a particular therapeutic dispensing application.

Handle 36 includes a pair of arms 48 that extend from proximal end 40. Arms 48 are flexibly connected to proximal end 40 and inverted inward. An inward bias of arms 48 facilitates engagement with a needle assembly 94 (FIG. 14) for positioning during dispensing of first therapeutic 32, as will be discussed. Arms 48 are oriented for receipt within carriage 24 and engagement with needle assembly 94. It is contemplated that arms 48 may be of variable length or resilient quality according to the particular therapeutic dispensing application.

Arms 48 form syringe arrestor 52 having a pair of cooperatively configured slots 54. Slots 54 are configured to engage a portion of needle assembly 94 to releasably lock needle assembly 94 in place relative to carriage 24. Thus, as carriage 24 engages, from an extended position (FIG. 16), for example, a body surface of the subject, carriage 24 retracts within handle 36, in the direction shown by arrow A, to a partially retracted position (FIG. 17) to expose a needle cannula 100 of needle assembly 94. During proximal movement of carriage 24, needle assembly 94 remains fixed in position by syringe arrestor 52. This configuration advantageously prevents undesired dispensing of first therapeutic 32 because plunger 30 is not undesirably forced into engagement with handle 36 during movement of carriage 24 to the partially retracted position.

Continued proximal movement of carriage 24 from the partially retracted position to the fully retracted position, force arms 48 in the direction shown by arrows B. This releases arrestor 52 and the portion of arms 48 adjacent slots 54. This allows arms 48 to slide along an inner surface of carriage 24 such that first therapeutic 32 can be dispensed, as will be discussed. It is contemplated that slots 54 may be disposed variously along the length of arms 48 according to the requirements of a particular therapeutic dispensing application.

Handle 36 includes a pusher 56 disposed adjacent proximal end 40 for engagement with plunger 30 to dispense first therapeutic 32 from therapeutic dispenser 20. Pusher 56 includes a receiving portion 58 configured for receiving plunger 30. Pusher 56 extends a suitable distance within channel 38 to drive plunger 30 through needle assembly 94 and effectuate dispensing of first therapeutic 32.

Handle 36 includes a pair of receiving cavities, such as, for example, safety lock pin receivers 60. Safety lock pin receivers 60 define a cavity within walls 46 and are configured to receive cap 37 for releasable engagement therewith. Safety lock pin receivers 60 include edges that catch and releasably lock and fixedly lock cap 37, as will be discussed, when handle 36 and cap 37 are engaged to enclose carriage 24. Safety lock pin receivers 60 are formed in each wall 46 but may alternatively be formed in a single wall 46 or other portions of handle 36. It is contemplated that the depth of safety lock pin receivers 60 may be of various degrees according to the particular therapeutic dispensing application. One or a plurality of safety lock pin receivers may be employed. It is further contemplated that cap 37 and handle 36 may be maintained in a releasable engagement by other means, such as, for example, clips, pins, etc.

Carriage detents 47 are disposed on a wall portion 47A of handle 36. Wall portions 47A extend distally from walls 46 and define a portion of safety lock pin receivers 60. Wall portion 47A is a thin walled portion that is rigidly disposed. Carriage detents 47 project into channel 38 for engagement with carriage 24. Carriage detents 47 releasably lock carriage 24 in the extended position (FIG. 16). It is contemplated that carriage detents 47 may be variously positioned along walls 46 and may releasably lock carriage 24 in various positions.

Handle 36 also includes a medication cavity 64 configured to support second therapeutic 34 (FIG. 16) such as, for example, pills, etc. Medication cavity 64 is a cavity which is substantially tubular or can conform to the portion of handle 36 depending on the requirements of a particular dispensing application. Medication cavity 64 is configured to receive second therapeutic 34 and, upon disengagement of cap 37 and base 36, is oriented such that second therapeutic 34 is easily removed therefrom. Medication cavity 64 may carry individually packaged medications or may itself be foil lined, etc. Medication cavity 64 may independently support second therapeutic 34 or be employed in such a manner as to support second therapeutic 34 in cooperation with cap 37. It is contemplated that medication cavity 64 does not support therapeutics and/or that cap 37 independently supports therapeutics, as will be discussed.

Figure 9:
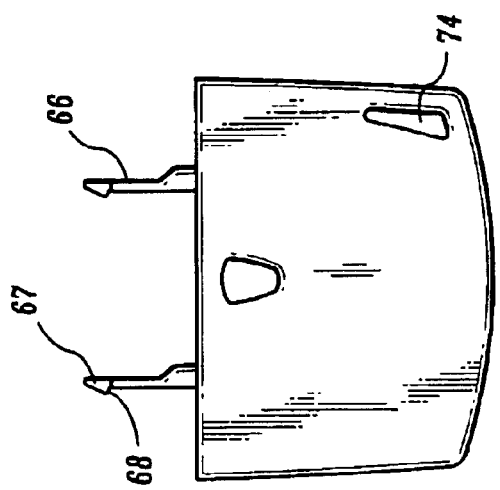
FIG. 9 is a reduced front view of the cap shown in FIG. 8.
Figure 8:
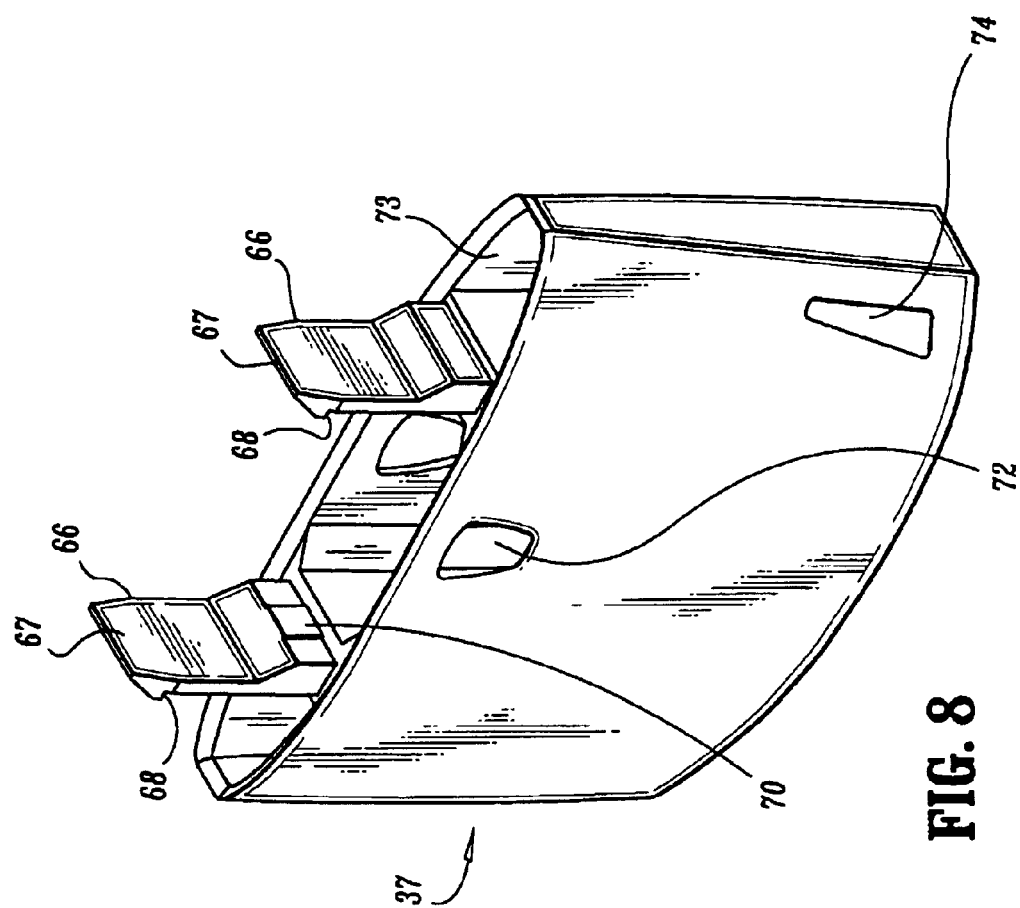
FIG. 8 is an enlarged perspective view of a cap of the therapeutic dispenser shown in FIG. 1.
Figure 9A:
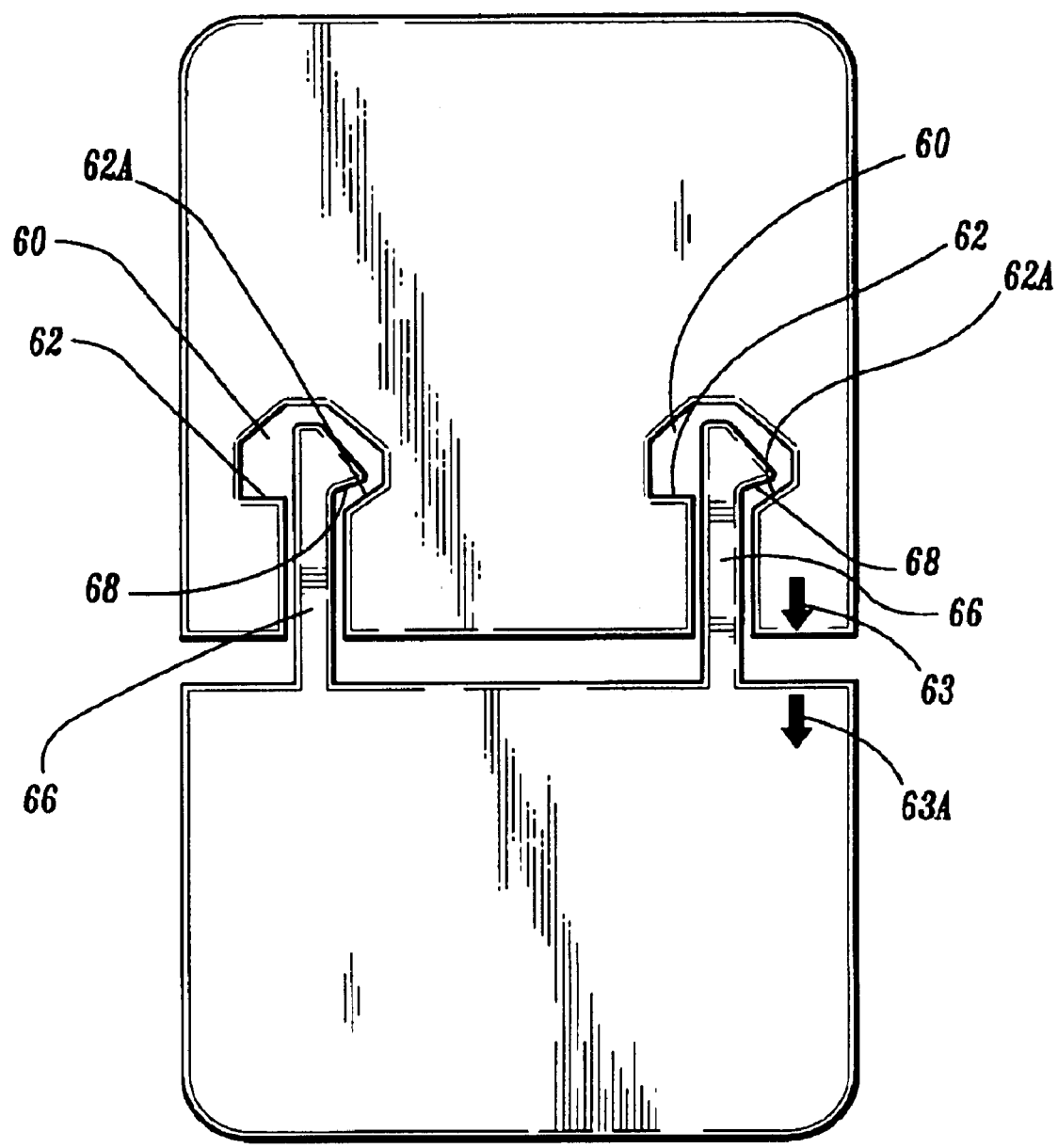
FIG. 9A is a front view, in part cross-section, of the therapeutic dispenser shown in FIG. 1, in a releasably locked position.

Referring to FIGS. 8 and 9, cap 37 includes safety lock pins 66 that project from cap 37 and are disposed to engage safety lock pin receivers 60 for releasably locking and fixedly locking cap 37 and handle 36. For assembly of cap 37 with handle 36, safety lock pins 66 are manipulated and enter safety lock pin receivers 60 as cap 37 is mated with handle 36, as shown in FIG. 9A. Safety lock pins 66 include edges 68 that engage edges 62A of safety lock pin receivers 60 in a frictional engagement and/or interference fit to releasably lock cap 37 with handle 36. In the initial assembled and releasably locking position, handle 36 and cap 37 include visual indicia, such as, for example, arrow 63 and arrow 63A, respectively, which demonstrate proper alignment of the components for releasable locking. Arrows 63, 63A are oriented in the same direction to indicate that handle 36 and cap 37 are releasably locked. Handle 36 and cap 37 similarly include visual indicia that demonstrates a fixedly locked condition, as will be discussed. For disengagement and release of cap 37 from handle 36, cap 37 is manipulated to overcome the frictional engagement and/or interference fit of edge 68 with edge 62A. Pins 66 are free to exit safety lock pin receivers 60. Cap 37 is released from handle 36 and therapeutic dispenser 20 is ready for use.

Figure 9B:
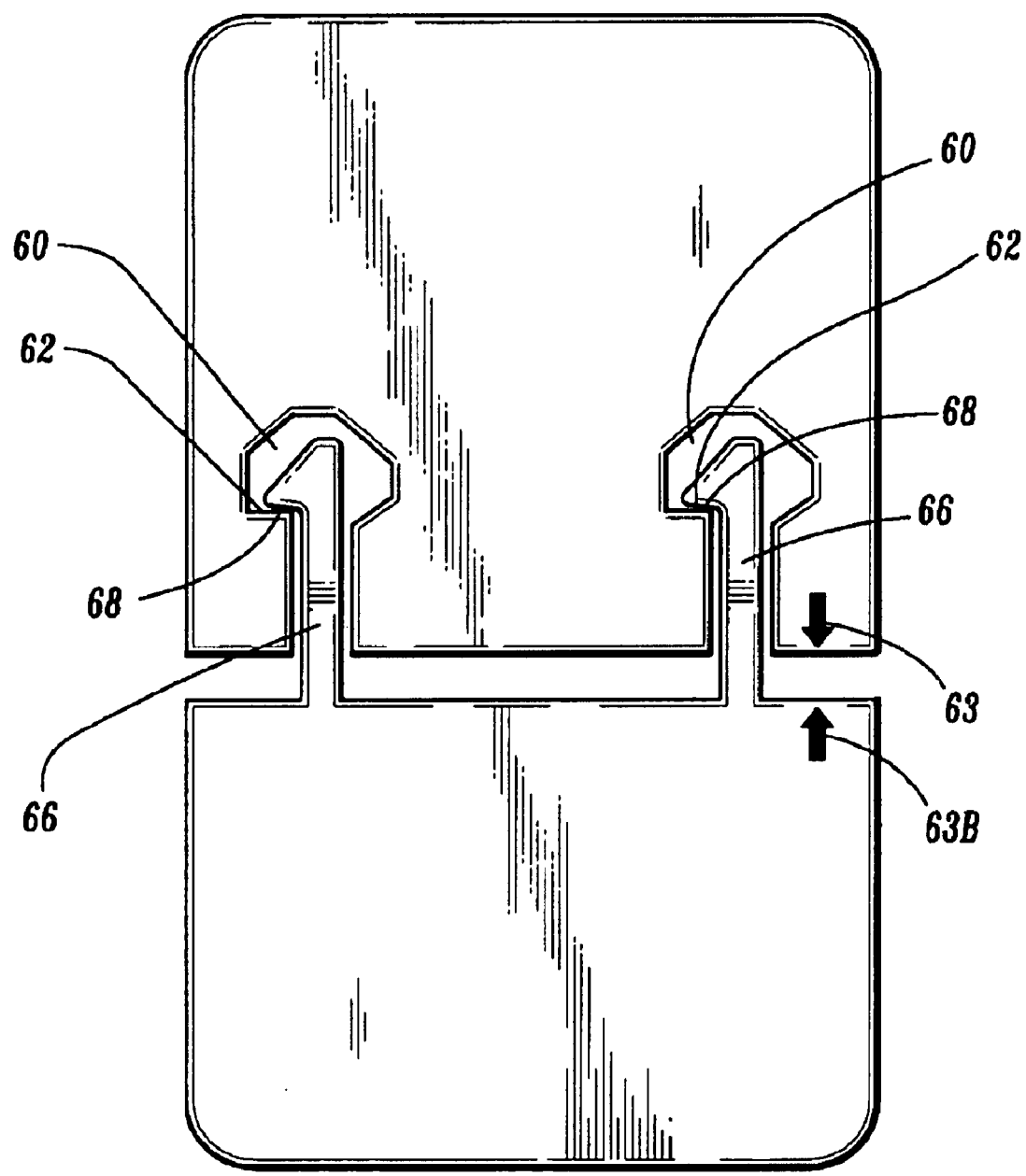
FIG. 9B is a front view, in part cross-section, of the therapeutic dispenser shown in FIG. 1, in a fixedly locked position.

Referring to FIG. 9B, subsequent to use of therapeutic dispenser 20, handle 36 can be assembled with cap 37 in a fixed or permanently locked condition. Cap 37 is oriented with handle 36 such that cap 37 is turned over (manipulated 180° relative to its orientation in the releasably locked condition). Cap 37 is manipulated so that safety lock pins 66 enter safety lock pin receivers 60. Edge 68 is disposed in fixed engagement with edge 62 and cap 37 is permanently locked with handle 36.

Arrow 63 is matched with visual indicia, such as, for example, arrow 63B (disposed on a side of cap 37 opposite to arrow 63A). Arrow 63, 63B are oriented in opposite directions to indicate that handle 36 and cap 37 are fixedly locked. It is contemplated that visual indicia may or may not be employed.

Cap 37 includes a fluid inspection window 72 which facilitates visual inspection of the presence and quantity of first therapeutic 32 disposed within carriage 24. A cavity, such as, for example, a lanyard slot 74 is defined within cap 37 and facilitates attachment to a cord, chain, etc., to facilitate portable carrying of therapeutic dispenser 20.

Cap 37 also includes a medication cavity 73 configured for support of second therapeutic 34. Medication cavity 73 is configured to receive second therapeutic 34, and, upon disengagement of cap 37 and handle 36, is oriented such that second therapeutic 34 is easily removed therefrom. Medication cavity 73 may carry individually packaged medications or may be foil lined, etc. Medication cavity 73 independently supports second therapeutic 34. Medication cavity 73 may cooperate with medication cavity 64 (FIG. 5) of handle 36, as discussed.

Figure 12:
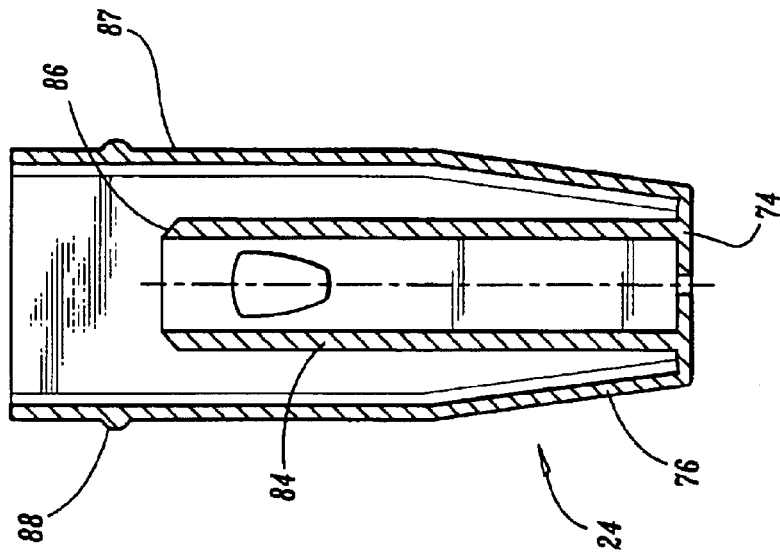
FIG. 12 is a cross-sectional view of the carriage taken along lines 12—12 of FIG. 11.
Figure 10:
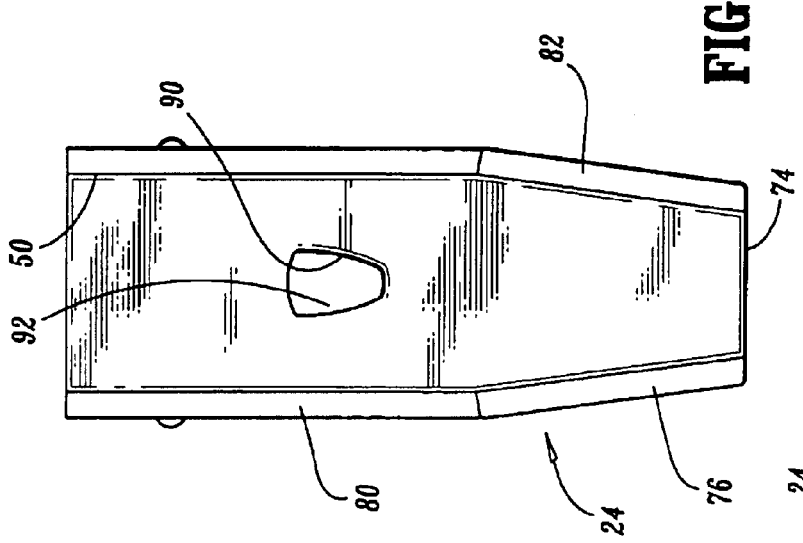
FIG. 10 is an enlarged front view of the carriage of the therapeutic dispenser shown in FIG. 1.
Figure 11:
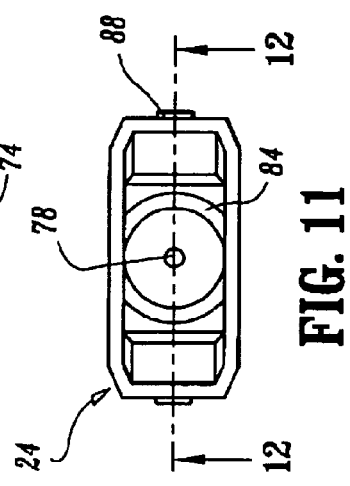
FIG. 11 is a top view of the carriage shown in FIG. 10.

Referring to FIGS. 10–12, carriage 24 is supported by handle 36 (FIG. 5) and includes a substantially non-flexible engagement surface 74 at a distal end 76 thereof. Engagement surface 74 defines an opening 78 configured for disposal of needle cannula 100 (FIG. 14) therein.

Carriage 24 is movable between an extended position (FIG. 16) relative to housing 22 (FIG. 1), a partially retracted position (FIG. 17) and a fully retracted position (FIG. 18), to dispense first therapeutic 32 and second therapeutic 34 from therapeutic dispenser 20 during a dispensing application.

Carriage 24 is substantially tubular and has a substantially rectangular cross-section, as shown in FIG. 11. Carriage 24 has a body portion 80 of generally uniform dimension and extending longitudinally. A nose portion 82 of cylinder 24 tapers inwardly toward distal end 76 to facilitate engagement with a targeted body surface of the subject.

Carriage 24 includes a cylinder, such as, for example, syringe shaft 84 for support of needle assembly 94 (FIG. 14), discussed below. Syringe shaft 84 is elongated in substantially coaxial alignment with carriage 24 and has a substantially cylindrical cross-section. It is contemplated that the component parts of carriage 24 may have various geometric configurations according to the particular requirements of a dispensing application. Syringe shaft 84 includes an arrest ramp 86 for engagement with arms 48 (FIG. 5) of handle 36. As discussed with regard to FIG. 5, as carriage 24 moves towards the fully retracted position to administer dispensing of first therapeutic 32, arrestor 52 is driven outwardly in the direction shown by arrows B. Arrestor 52 slides over arrestor ramp 86 and along the outer surface of syringe shaft 84. This facilitates engagement of plunger 30 with pusher 56 to enable dispensing of first therapeutic 32.

An outer surface 87 of body portion 80 includes carriage arrestor detents 88 that engage carriage detents 47 (FIG. 5) of walls 46. Arrestor detents 88 engage carriage detents 47 to releasably retain or lock carriage 24 in the extended position during a therapeutic dispensing procedure. Carriage 24 includes a top fluid inspection window 90 of body portion 80 and a bottom fluid inspection window 92 of syringe shaft 84 which allow visual inspection of the presence and quantity of first therapeutic 32 disposed within carriage 24. Windows 90 and 92 are formed with carriage 24 and through to syringe shaft 84 in an abutting relationship. It is contemplated that the inspection windows may be monolithically or separately formed with carriage 24 and syringe shaft 84 or variously disposed thereabout.

Engagement surface 74 has a substantially rectangular configuration and is substantially non-flexible for engagement with a body surface of the subject. Upon engagement from the extended position (FIG. 16), the rigidity of engagement surface 74 causes carriage 24 to retract within handle 36 to the partially retracted position (FIG. 17) and then to the fully retracted position (FIG. 18) to dispense first therapeutic 32 from therapeutic dispenser 20, as will be discussed in more detail below. It is contemplated that engagement surface 74 may be alternatively configured, such as, for example, convex, concave, etc., according to the requirements of the particular therapeutic dispensing application.

Figure 13:
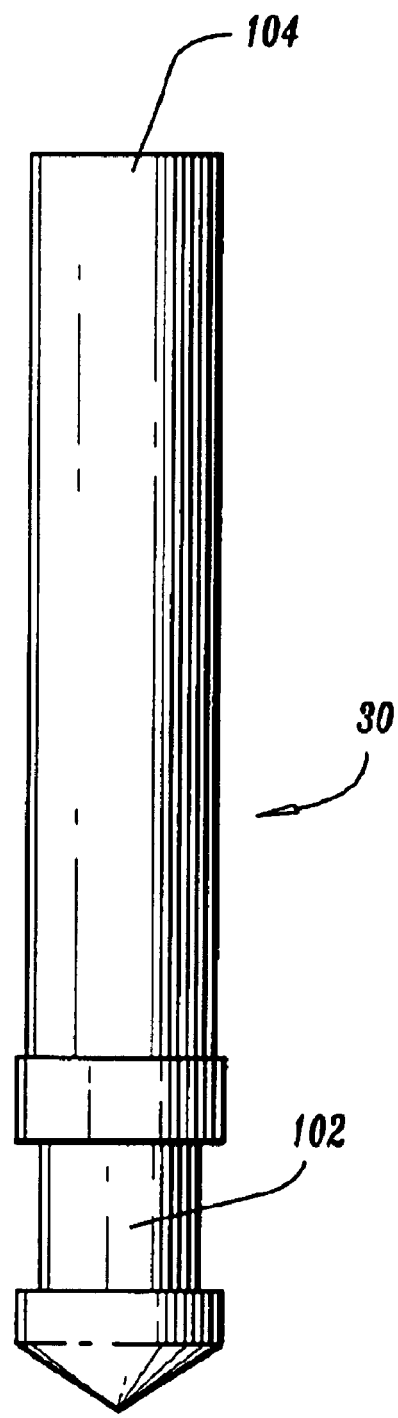
FIG. 13 is a front view of a plunger of the therapeutic dispenser shown in FIG. 1.
Figure 14:
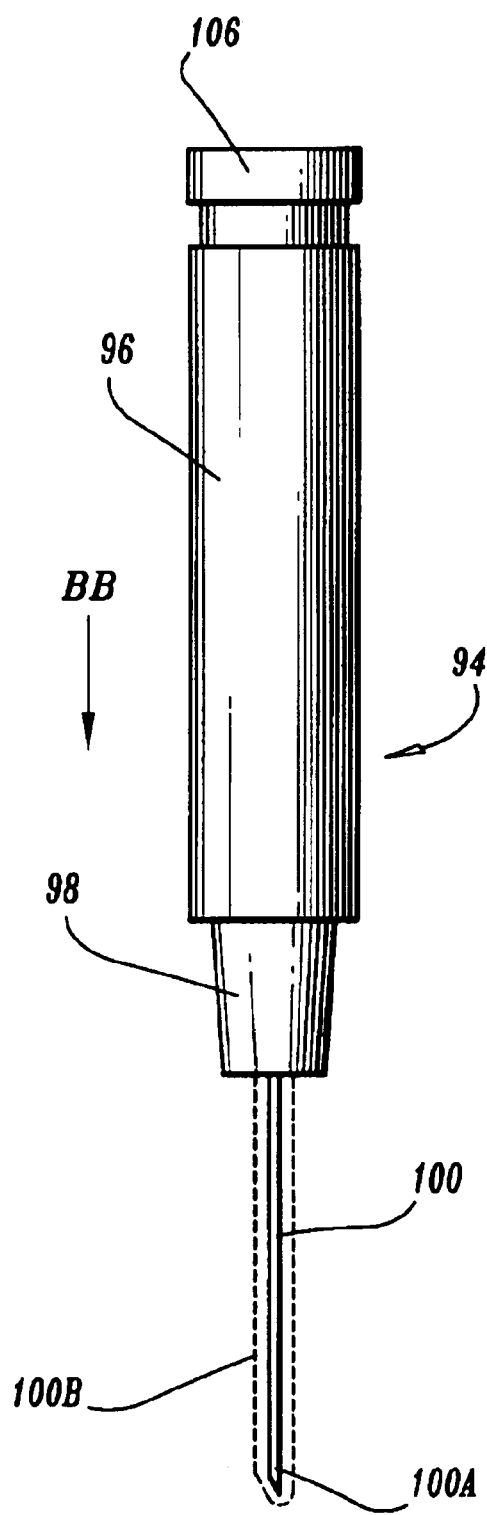
FIG. 14 is a front view of a needle assembly of the therapeutic dispenser shown in FIG. 1.

Referring to FIGS. 13 and 14, a needle, such as, for example, a needle assembly 94 is supported by syringe shaft 84 (FIG. 12). Needle assembly 94 includes a barrel 96 which supports plunger 30 and contains a first therapeutic 32 (not shown). Needle assembly 94 includes a needle hub 98 that engages an interior surface of syringe shaft 84 for disposal therein. A needle cannula 100 extends from needle hub 98 through opening 78 of engagement surface 74 to engage a body surface to dispense first therapeutic 32 for administration of an injection. Needle cannula 100 has a sharpened distal tip 100A configured to penetrate a body surface of the subject. A flexible sheath 100B encloses a portion of needle cannula 100 projecting from needle hub 98. Flexible sheath 100B may cover variable amounts of needle cannula 100. Flexible sheath 100B maintains sterility and prevents accidental needle stick. Flexible sheath 100B is made from an elastomeric material such as, rubber, etc. and may be transparent. Flexible sheath 100B may be configured as a condom, flexible membrane, etc. Upon engagement with the body surface of a subject, distal tip 100A pierces through flexible sheath 100B and into the body surface.

Barrel 96 includes an arrestor slot 106 configured to engage slots 54 of arrestor 52 (FIG. 5) to maintain needle assembly 94 in a fixed position during movement of carriage 24 to the partially retracted position (FIG. 17), as discussed. Upon engagement of engagement surface 74 with a body surface, carriage 24 and correspondingly barrel 96 are caused to move proximally within handle 36. This movement releases slots 54 from engagement with arrestor 106 allowing free slidable movement of barrel 96. Arms 48 are released from fixed engagement with barrel 96 and move along syringe shaft 84, as discussed.

Figure 25:
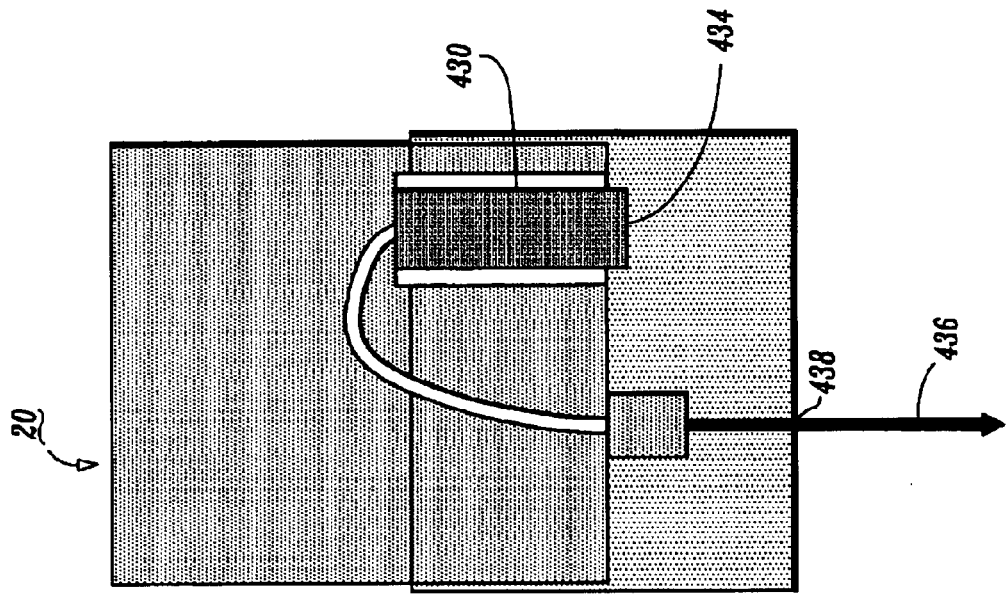
FIG. 25 is a front view of the therapeutic dispenser shown in FIG. 24 in an engaged position.
Figure 24:
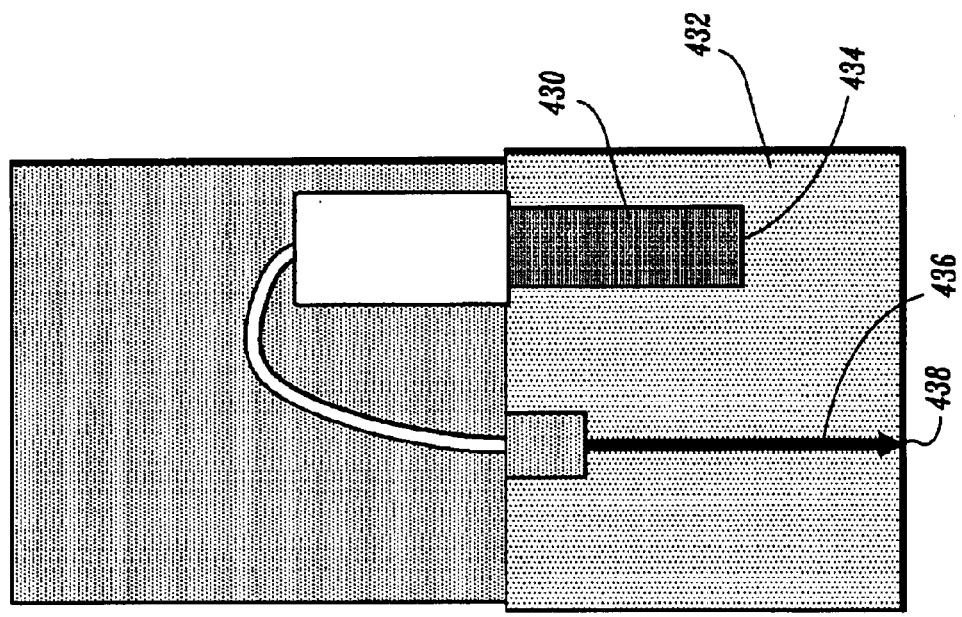
FIG. 24 is a front view of an alternate embodiment of the therapeutic dispenser in a disengaged position.

Upon release of arrestor 52, carriage 24 is forced toward the fully retracted position (FIG. 18), whereby plunger 30 is forced into engagement with pusher 56 (FIG. 5). Plunger 30 includes an elastomeric sealing member 102 that is slidably received by an interior surface of barrel 96. Upon engagement of a pusher end 104 of plunger 30 with receiver 58 of pusher 56 sealing member 102 drives through barrel 96, in the direction shown by arrow BB, such that first therapeutic 32 is expelled from barrel 96 via needle cannula 100 into a body surface of the subject, as will be discussed below. In an alternate embodiment, similar to those discussed, as shown in FIGS. 24 and 25, therapeutic dispenser 20 has a plunger 430 directed towards the subject and disposed in a carriage 432 (FIG. 24). Upon engagement of carriage 432 with the subject, a plunger actuator 434 causes plunger 430 to expel a therapeutic through a needle cannula 436. As carriage 432 is driven towards the engaged position (FIG. 25), needle cannula 436 passes through a hole 438 of carriage 432 for injection with the subject.

Figures 26, 27:
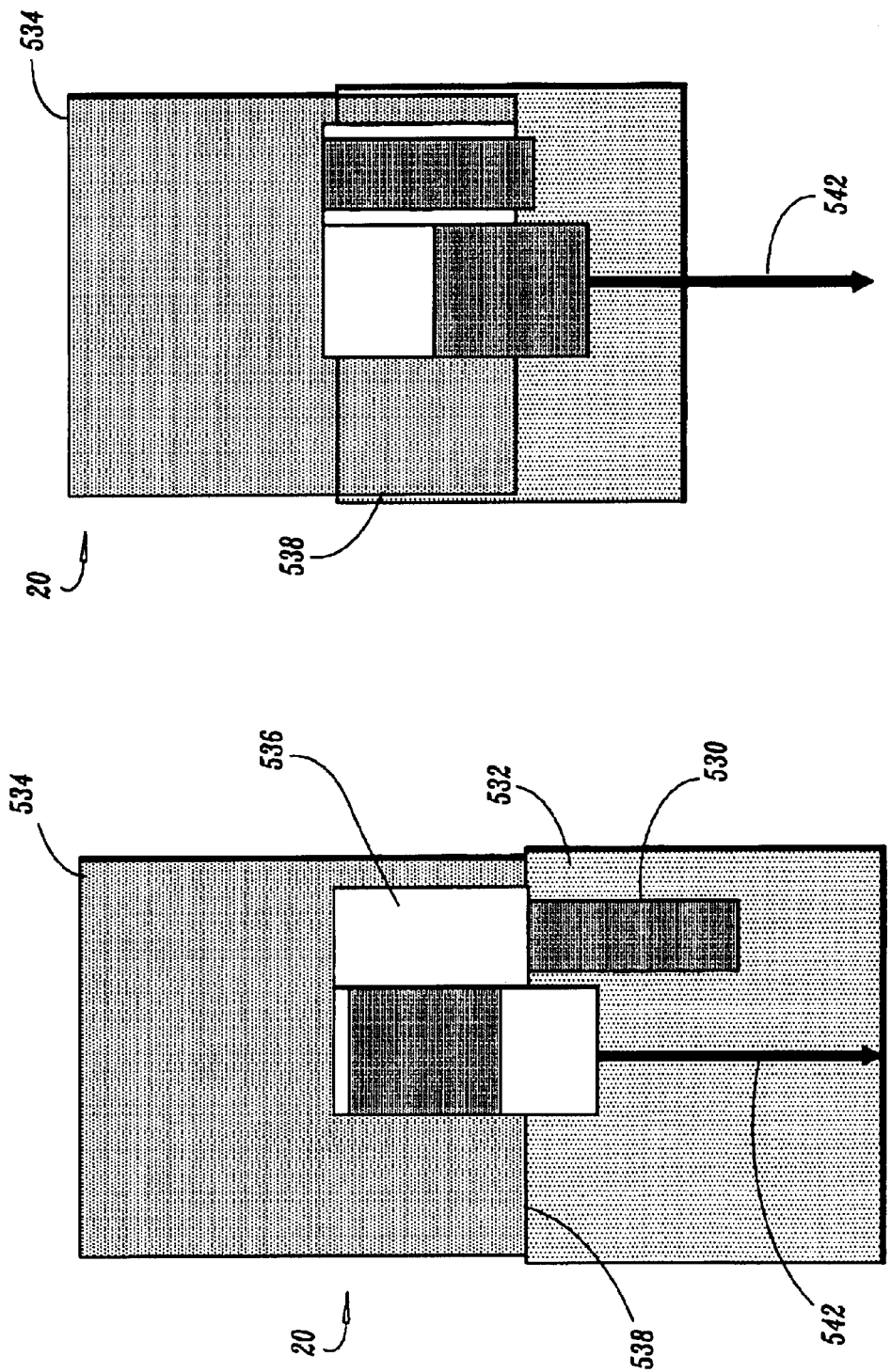
FIG. 26 is a front view of an alternate embodiment of the therapeutic dispenser in a disengaged position.
FIG. 27 is a front view of the therapeutic dispenser shown in FIG. 26 in an engaged position.
Figure 28:
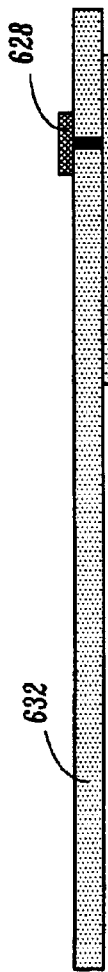
FIG. 28 is a top view of a portion of an alternate embodiment of the therapeutic dispenser.
Figure 29:
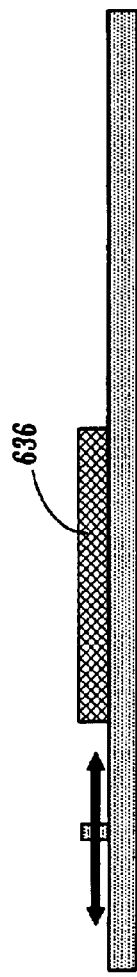
FIG. 29 is a bottom view of a portion of the therapeutic dispenser shown in FIG. 28.
Figure 30:
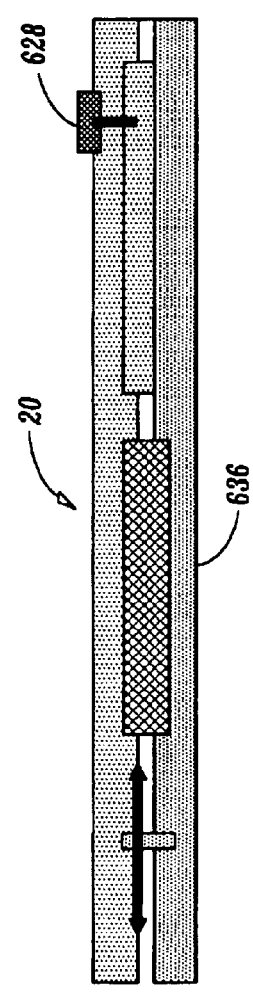
FIG. 30 is a top view of the therapeutic dispenser shown in FIGS. 28 and 29 in a disengaged position.
Figure 31:
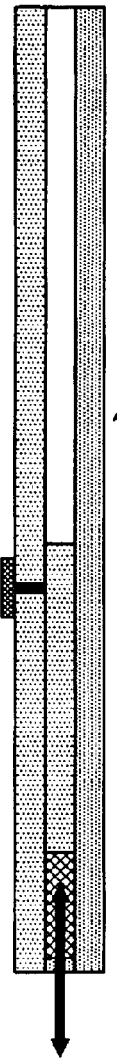
FIG. 31 is a top view of the therapeutic dispenser shown in FIGS. 28 and 29 in an engaged position.

In another alternate embodiment, similar to those discussed, as shown in FIGS. 26 and 27, therapeutic dispenser 20 has a plunger 530 directed towards the subject and disposed in a carriage 532 (FIG. 26). Upon engagement of carriage 532 with the subject, plunger 530 is forced towards a handle 534. A liquid 536 contained within handle 534 and moving in a plunger-like operation, drives a second plunger 538 towards the subject. Second plunger 538 forces therapeutics, contained within a reservoir 540, through a needle cannula 542 for injection within the subject.

In yet another alternate embodiment, similar to those discussed, as shown in FIGS. 28–31, therapeutic dispenser 20 has a thumb slide 628 connected to a plunger 630. Plunger 630 is supported between a top card 632 and a bottom cord 634. Manipulation of thumb slide 628, in the direction shown by arrow Y (FIG. 30), causes plunger 630 to engage a flexible therapeutic container 636. This forces therapeutics contained in flexible therapeutic container 636 through a needle cannula 638 for injection within the subject.

The components of therapeutic dispenser 20 are assembled in accordance with the description detailed above although variations may be made thereto in accordance therewith and conforming to the requirements of a particular therapeutic dispensing application. Operation of a therapeutic dispenser, in accordance with the principles of the present disclosure, similar to that described with regard to FIGS. 1–14, will now be discussed. Initially, proper preparation and sterilization of those components of therapeutic dispenser 20 requiring such preparation is conducted.

Referring to FIGS. 15–18, for example, if a subject (not shown) believes they are suffering from the early signs of a heart attack, the subject manipulates and removes therapeutic dispenser 20, which has a card configuration, as shown in FIG. 15, from a shirt or pant pocket (not shown). Therapeutic dispenser 20 has instructional indicia 110 mounted to an outer surface 112. Instructional indicia 110 provides the subject with instructions for the operating procedure of therapeutic dispenser 20 and the administration of the therapeutics, medications, etc. contained therewith, similar to that described. It is contemplated that instructional indicia 110 represents instructions according to a particular dispensing application.

Instructional indicia 110 is separated into, for example, steps for use of therapeutic dispenser 20. Windows 72, 90 and 92 provide a visual indication that first therapeutic 32 is disposed within carriage 24. It is contemplated that windows 72, 90 and 92 may provide a visual indication that a particular therapeutic is defective. A first step may include contacting an emergency facility or a primary physician. A second step may include manipulation of therapeutic dispenser 20 such that cap 37 is released from locking engagement with handle 36, as shown in FIG. 16 and described above. Safety lock pins 66 exit safety lock pin receivers 60 and carriage 24 is disposed in the extended position. Carriage arrestor detents 88 (FIG. 12) engage carriage detents 47 (FIG. 5) to releasably lock carriage 24 in the extended position. Needle cannula 100 does not project through opening 78. It is contemplated that needle cannula 100 may project therethrough in the extended position.

A third step may include removing second therapeutic 34, such as, pills, etc., from medication cavities 64 and 73.

Second therapeutic 34 may be dispensed and administered before or after administration of first therapeutic 32, according to the particular dispensing application. Step 4 includes manipulating handle 36 to orient engagement surface 74 of carriage 24 adjacent a body surface of the subject and on target to inject first therapeutic 32. Engagement surface 74 is brought into contact with the body surface. The subject applies a force, in the direction shown by arrow C, to a surface 114 of handle 36. The force disengages carriage arrestor detents 88 and carriage detents 47 allowing slidable movement of carriage 24 relative to handle 36. Syringe arrestor 52 releases plunger 30 for slidable movement thereof within barrel 96. Needle cannula 100 passes through opening 78 and penetrates the body surface. Carriage 24 retracts, in the direction shown by arrow D, and is disposed in the partially retracted position, as shown by FIG. 17.

Continued application of the force, in the direction shown by arrow C, causes pusher end 104 (FIG. 13) of plunger 30 to engage receiver 58 (FIG. 5) of pusher 56. Elastomeric sealing member 102 is slidably driven through barrel 96 expelling first therapeutic 32 from barrel 96. First therapeutic 32 flows through needle cannula 100 and is injected into the body surface for administration to the subject. Therapeutic dispenser 20 may be discarded after use.

It is contemplated that therapeutic dispenser 20 may be employed without injectable therapeutics. For example, therapeutic dispenser 20 may be configured to support one or a plurality of therapeutics, such as, oral, topical, etc. The therapeutics are supported in medication cavities, similar to medication cavities 64, 73 described with regard to FIGS. 1–18. The therapeutics may also be supported in a cavity, similar to channel 38 described with regard to FIG. 5. As described, cap 37 is disengaged from handle 36 and the therapeutics, in oral, topical, etc. form are dispensed from the cavities of therapeutic dispenser 20.

Referring to FIG. 19, the plurality of therapeutics may be dispensed according to another embodiment of therapeutic dispenser 20, similar to that described above, such as, for example, a heartcard which has an overall card configuration. As shown in FIG. 19A, the heartcard has a bubble/foil pack configuration 112 to enclose a first therapeutic 132, such as, for example, aspirin, and a second therapeutic 134, such as, for example, nitroglycerin. As discussed, other therapeutics are also contemplated. The heartcard includes instructional indicia 110 disposed thereon. Instructional indicia 110 provides instructions printed on the front or backside thereof for dispensing the therapeutics. It is contemplated that instructional indicia 110 may include audio, visual and tactile indicia. For example, the instructions, in the case of cardiac distress may include:

IF YOU ARE EXPERIENCING CHEST PAIN

Step 1: CALL 911 or your Primary Medical Doctor;

Step 2: TAKE ASPIRIN (chew or swallow);

Step 3: Take $1^{st}$ Dose of Nitroglycerin Sublingual (under your tongue). If there is no relief of chest pain within 5 minutes then;

Step 4: Take $2^{nd}$ Dose of Nitroglycerin Sublingual (under your tongue) If there is still no relief of chest pain within 5 minutes then;

Step 5: Take $3^{rd}$ Dose of Nitroglycerin Sublingual (under your tongue) *Continue at all times to contact 911 or your primary care physician In an alternate embodiment, instructional indicia 110 contains an audio chip that broadcasts the instructions in a manner which can be heard by the subject or a bystander, when product dispenser 20 is manipulated in a particular manner. It is contemplated that tactile may include Braille, etc.

Figure 22:
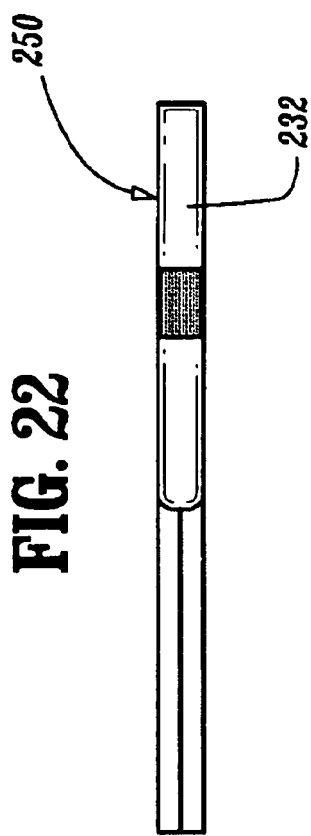
FIG. 22 is a side view of another alternate embodiment of the therapeutic dispenser.
Figure 23:
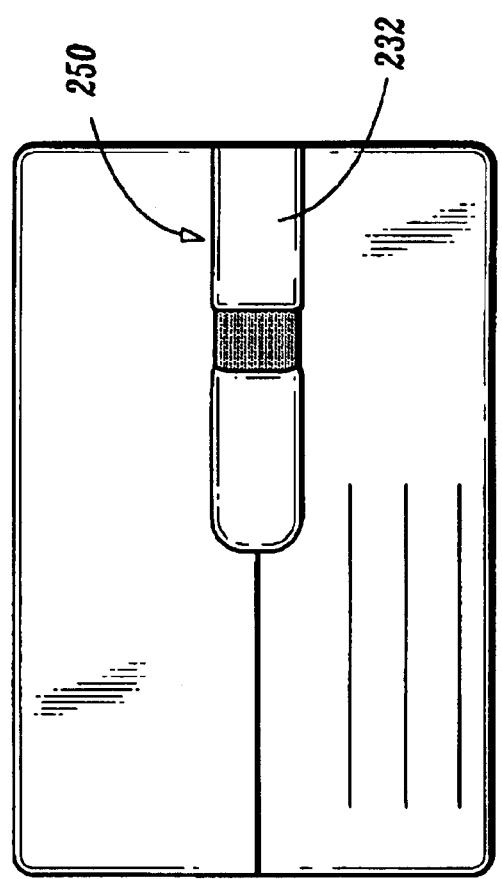
FIG. 23 is a front view of the therapeutic dispenser shown in FIG. 22.

Referring to FIGS. 20 and 21, in another alternate embodiment, therapeutic dispenser 20, similar to those described, has a peel away liner 222 which is removed for use thereof. In use, a needle cannula 224 which is removably attached to therapeutic dispenser 20 via adhesive or the like is removed. Needle cannula 224 is attached to a therapeutic pachreading, clips, etc. Therapeutic pack 226 is a flexible pack (made of foil, etc.) which can be squeezed to dispense a therapeutic 232, such as a sterile liquid medication, through needle cannula 222 to administer subcutaneously and/or for intramuscular injections. The therapeutics may be dispensed by applying pressure to the bubble/foil pack and forcing the therapeutics through a frangible portion of therapeutic dispenser 20. The therapeutics are then administered orally to the subject. Therapeutic dispenser 20 includes instructional indicia 210, similar to that described. In an emergency situation, needle cannula 224 is removed and attached to therapeutic pack 226 allowing for a subcutaneous or intramuscular injection. Therapeutic 232 is manually squeezed or forced through needle cannula 224 for administration to the subject. Alternatively, as shown in FIGS. 22 and 23, peel away liner 222 (not shown) may be removed to expose a syringe 250 which is pre-filled with therapeutic 232. This embodiment of therapeutic dispenser 20 has a card configuration employed similar to that described with regard to FIGS. 1–18. Additional therapeutics may be administered via a foil-pack, etc.

It will be understood that various modifications may be made to the embodiments disclosed herein. Therefore, the above description should not be construed, as limiting, but merely as exemplification of the various embodiments. Those skilled in the art will envision other modifications within the scope and spirit of the claims appended hereto.

What is claimed is:

1. A therapeutic dispenser comprising:

a handle defining a channel and a pair of arms defining a syringe arrestor extending from a proximal end thereof; said handle including a pusher disposed adjacent said proximal end, said handle defining a pair of pin receiving cavities;

a carriage supported by said handle and including a substantially non-flexible engagement surface at a distal end thereof, said engagement surface defining an opening;

a needle assembly supported by said carriage, said needle assembly including a barrel supporting a plunger and containing a first therapeutic, said needle assembly further including a needle hub having a needle cannula extending through said opening of said engagement surface; and a cap including a pair of pins that are releasably engageable with said pair of pin receiving cavities of said handle to enclose said carriage, said handle and said cap cooperating to define a cavity configured to support a second therapeutic, wherein said engagement surface is configured to engage a body surface such that said plunger engages said pusher to dispense said first therapeutic from said barrel through said needle cannula into said body surface.

2. A therapeutic dispenser comprising:

a handle having distal end and a channel extending internally in said handle from said distal end;

a syringe arrestor disposed in said channel;

a needle assembly having a barrel releasably retained in said channel by said syringe arrestor, a plunger extending proximally from said barrel, a needle hub extending distally from said barrel and a needle extending distally from said needle hub; and a carriage disposed in said channel and movable from an extended position wherein said carriage protrudes from said distal end of said handle to a refracted position;

said carriage enclosing said needle when said carriage is in said extended position;

said carriage engaging said syringe arrestor to release said barrel when said carriage is partially retracted.

3. The therapeutic dispenser according to claim 2 wherein said carriage includes an distal wall which abuts said needle hub when said carriage is partially retracted to move said barrel distally with said carriage as said carriage is further retracted, wherein said plunger is thereby pushed into said barrel.

4. The therapeutic dispenser according to claim 2 wherein said handle includes a at least one medication cavity for storing additional therapeutics.

5. The therapeutic dispenser according to claim 2 wherein said syringe arrestor comprises at least one movable arms having a slot adapted to engage said barrel, and wherein said carriage includes an arrest ramp adapted to deflect said movable arm away from said barrel.

6. The therapeutic dispenser according to claim 2 wherein said carriage includes detents adapted for releasable retaining said carriage in said extended position relative to said handle.

7. The therapeutic dispenser according to claim 2 further comprising a cap fitting over said carriage when said carriage is in said extended position, said cap being releasably attachable to said handle.

8. The therapeutic dispenser according to claim 7 wherein said cap includes at least one pin engagable with said housing;

wherein said cap includes a first orientation and a second orientation relative to said housing;

wherein said at least one pin is adapted to releasably lock said cover to said handle when said cap is in a first orientation, and to fixedly lock said cover to said handle when said cap is in a second orientation.

* * * * *